United States Patent [19]

Cordes et al.

[11] Patent Number: 5,711,962
[45] Date of Patent: Jan. 27, 1998

[54] TRANSDERMAL THERAPEUTIC SYSTEM FOR APPLICATION OF PHARMACEUTICALS ONTO THE SKIN

[75] Inventors: Günter Cordes, Leichlingen, Germany; Lucio C. Rovati, Monza, Italy

[73] Assignee: Rotta Research Laboratorium S.p.A., Milan, Italy

[21] Appl. No.: 619,555

[22] PCT Filed: Sep. 30, 1994

[86] PCT No.: PCT/EP94/03269

§ 371 Date: Mar. 27, 1996

§ 102(e) Date: Mar. 27, 1996

[87] PCT Pub. No.: WO95/09618

PCT Pub. Date: Apr. 13, 1995

[30] Foreign Application Priority Data

Oct. 1, 1993 [DE] Germany ............ 43 33 595.0

[51] Int. Cl.⁶ .................. A61L 15/16; A61F 13/02

[52] U.S. Cl. .............. 424/447; 424/448; 424/449
[58] Field of Search .................. 424/447, 448, 424/449

[56] References Cited

U.S. PATENT DOCUMENTS 5,128,124  7/1992  Fankhauser et al. ............ 424/449
5,132,115  7/1992  Wolter et al. .................. 424/448

*Primary Examiner*—Joseph L. Schofer
*Assistant Examiner*—Kathryne E. Shelborne
*Attorney, Agent, or Firm*—Kane, Dalsimer, Sullivan, Kurucz, Levy, Eisele and Richard

[57] ABSTRACT

Transdermal therapeutic systems containing as active ingredients oestradiol and norethisterone acetate have added thereto octyldodecanol to reduce or avert crystal formation after storage. The use of octyldodecanol thus makes it possible to produce a storage-stable system with the active ingredients oestradiol and norethisterone acetate with a high thermodynamic activity.

6 Claims, No Drawings

TRANSDERMAL THERAPEUTIC SYSTEM FOR APPLICATION OF PHARMACEUTICALS ONTO THE SKIN

BACKGROUND OF THE INVENTION

1. Field of the Invention

The present invention relates to a transdermal therapeutic system (TTS) for application of pharmaceuticals onto the skin, specifically of oestradiol and norethisterone acetate.

2. Brief Description of Related Art

TTS are used, inter alia, for administering certain hormones to people in order to raise the hormone level which declines during the course of ageing. In general, a plaster of this type consists of a backing sheet, of an adhesive with the active ingredients and ancillary substances, of an optional further adhesive in the form of a layer in order to increase the adhesion properties and, finally, of a protective sheet which is pulled off and removed before the plaster is used. The active ingredients pass through the skin into the body.

In many cases it is difficult when active ingredients are administered from TTS to achieve a sufficiently high flux through the skin and thus a sufficiently high blood level. This problem is countered either by adding suitable enhancers which improve the permeability of the skin for the active ingredient, or the concentration of active ingredient in the adhesive or in the matrix containing the active ingredient is chosen to be as high as possible. The intention of the high concentration of active ingredient is to achieve high thermodynamic activity and thus make greater permeation through the skin possible. These measures mean that the solubility or saturation limit of the active ingredient in the matrix is approached and, moreover, may be exceeded. Because this limit cannot always be accurately established or complied with, and the attempt to choose a concentration of active ingredient which is as high as possible may lead to it being in or above the region of the limit, signs of crystallization may occur after a few weeks or months of storage of TTS. Such signs of crystallization are a well-known phenomenon for skilled workers in the TTS area.

DE-A-4 020 144 describes, for example, a TTS system for various active ingredients such as oestradiol and norethisterone acetate (page 4, lines 27 to 28), in which case the self-adhesive matrix layer is provided by a polyacrylate adhesive (claim 1). The enhancer or penetration promoter proposed is, for example, n-dodecanol (page 5, line 53). The crystallization problem is not mentioned. DE-A-3 933 460 relates to a TTS for hormones such as oestradiol and norethisterone (page 4, lines 26 to 51), and homo- and/or copolymers with at least one derivative of acrylic or methacrylic acid are provided as adhesives (page 3, para. 3 et seq.). An expedient embodiment may contain substances which delay or prevent the crystallization of the active ingredient and which are present in a concentration of from 0.1 to 20% by weight, mention being made of phthalic esters, adipic esters, mono-, di- and triglycerides, esters of higher fatty acids, long-chain alcohols and derivatives thereof, derivatives of nonylphenol and of octylphenol, derivatives of fatty acids, derivatives of sorbitol and of mannitol, nonionic surfactants, polyoxyethylene alkyl ethers, derivatives of castor oil, sitosterol and polyvinylpyrrolidone as crystallization retardants (page 3, para. 2 and page 4, para. 2). DE-A-3 810 896 proposes a TTS in which, for example, oestradiol and norethisterone acetate are provided in a reservoir. Penetration improvers are also mentioned (page 3, line 39 and page 5, line 50 et seq.). Crystallization problems are not mentioned. U.S. Pat. No. 5,198,223 relates to a transdermal therapeutic system for, for example, oestradiol (column 7, penultimate paragraph), in which penetration enhancers can also be provided (column 6, para. 4 et seq.). Crystallization problems are not mentioned. EP-A-0 416 842 provides a transdermal therapeutic matrix system for, for example, oestradiol (page 4, line 2), it being emphasized that penetration enhancers can be omitted if the proposed matrix is used (page 3, lines 33 to 37). Crystallization problems are not mentioned. WO-A-93/10 772 describes an oestradiol-containing transdermal therapeutic system for whose adhesive acrylate copolymers are proposed (claims 1 and 2). Crystallization inhibitors are not mentioned. However, the known system is intended by its special design to avert crystallization.

SUMMARY OF THE INVENTION

It is an object of the present invention to provide a transdermal therapeutic system for the application of oestradiol and norethisterone acetate, with which, while the concentration of active ingredient is high, signs of crystallization can be averted even more satisfactorily.

The object on which the invention is based is now achieved by a transdermal therapeutic system which comprises a backing sheet
an acrylate-based adhesive as matrix in which
dissolved oestradiol and norethisterone acetate (NETA) are present as active ingredients and
octyldodecanol is present,
where appropriate another layer of an adhesive and
a protective sheet,
or consists of these components.

The present invention thus provides for the addition of a particular ancillary substance, namely octyldodecanol, to the polymer adhesive composition with the active ingredients dissolved therein, in order in this way to reduce signs of crystallization of the active ingredients even after storage. It is possible in this way to maintain a high thermodynamic activity without having to accept the risk of crystal formation. Octyldodecanol is commercially available as Eutanol G.

DETAILED DESCRIPTION OF THE PREFERRED EMBODIMENTS OF THE INVENTION

The backing sheet in the TTS according to the invention can consist of polyethylene terephthalate.

The acrylate-based adhesive to be used according to the invention can have been prepared by free-radical copolymerization of 2-ethylhexyl acrylate and/or
methyl acrylate and/or
acrylic acid and/or
vinyl acetate and/or hydroxyethyl acrylate and
where appropriate up to 2% of other substances.

For example, the acrylate-based adhesive can have been prepared by free-radical copolymerization of 2-ethylhexyl acrylate in an amount of from 50 to 70 and, in particular, 55 to 65, %,
methyl acrylate in an amount of from 24 to 32%,
acrylic acid in an amount of from 2 to 8%,
vinyl acetate in an amount of from 2 to 10% and
hydroxyethyl acrylate in an amount of from 0.5 to 3% (in each case based on the weight of the matrix).

Reference may also be made to the entire contents of WO-A-93/10 772 for the acrylate-based adhesive which can be used according to the invention.

According to a preferred embodiment, the acrylate-based adhesive which can be used according the invention can comprise a mixture of two or more adhesives as have been described above.

According to a preferred embodiment, one $cm^2$ of the transdermal therapeutic system according to the invention can comprise the following components:

0.05 to 0.5 mg of oestradiol, 0.5 to 1.5 mg of norethisterone acetate, 0.1 to 0.5 mg of octyldodecanol and 5 to 12 mg of an acrylate-based adhesive.

The protective sheet of the TTS according to the invention can consist of polyethylene terephthalate.

It is emphasized once again that the active ingredients in the transdermal therapeutic system according to the invention are present in dissolved form and not in crystalline form.

EXAMPLE 1

14 g of oestradiol and 92 g of norethisterone acetate are dissolved with stirring in 1,200 g of ethyl methyl ketone. While continuing to stir, 23.7 g of octyldodecanol are added. Then 360 g of a 51 percent solution (W/V) of a first acrylate copolymer (Durotac 280-2287 from National Starch Chemical B.V. (Zutphen/Netherlands)) and 2,000 g of a 37 percent solution of another acrylate copolymer (Durotac 326-1753 from National Starch Chemicals B.V.) are added and dissolved by stirring. After a homogeneous solution has been produced, it is spread onto a siliconized polyester sheet (100 μm). The solvent is then allowed to evaporate, warming to about 40° C. where appropriate, and the adhesive side is covered with a polyester sheet (15 μm). The individual TTS are punched out in the required size in a conventional way, for example in a size of from 20 to 50 $cm^2$.

EXAMPLE 2 AND COMPARATIVE EXAMPLE 1

The rate of crystallization of the two active ingredients can be greatly increased by storage at 40° C. and 75% relative humidity. Such an extreme treatment of the polymer matrix allows it to be shown after a relatively short time that a TTS according to the invention with an octyldodecanol content is superior to a TTS without octyldodecanol. For this comparison, Example 1 was repeated in the following way.

Comparative Example 1

5.8 mg of oestradiol 35.8 mg of norethisterone acetate 362.0 mg of polyacrylate mixture

Comparative Example 2

5.8 mg of oestradiol 35.8 mg of norethisterone acetate 362.0 mg of polyacrylate mixture 9.3 mg of octyldodecanol

TABLE 1

|  | Comparative Example 1 | Example 2 |
| --- | --- | --- |
| Storage at 40° C./75% RH | 2 weeks | 2 weeks |
| Number of crystals/$cm^2$ | 27 | 5 |
| Crystal size | 0.4 mm | 0.25 mm |

Comparison of the examples proves that octyldodecanol distinctly reduces the size and number of the crystals in the adhesive matrix under the test conditions. On storage at room temperature crystals form only after a far longer time, and they would be entirely absent in Example 2.

We claim:

1. A transdermal therapeutic system, which comprises;

a backing sheet having deposited thereon a matrix which is an acrylate-based adhesive, said adhesive having dissolved therein as active therapeutic ingredients (a) oestradiol and norethisterone acetate; and (b) octyldodecanol;

said adhesive having been prepared by free-radical copolymerization of (i) 50 to 70 percent by weight of 2-ethylhexyl acrylate;

(ii) 20 to 40 percent by weight of methyl acrylate;

(iii) 2 to 8 percent by weight of acrylic acid;

(iv) 2 to 10 percent by weight of vinyl acetate; and (v) 0.5 to 3 percent by weight of hydroxyethyl acrylate.

2. The system of claim 1 which further comprises a protective covering sheet.

3. The system of claim 8 wherein the adhesive was prepared by the free-radical copolymerization of, (i) 55 to 65 percent by weight of 2-ethylhexyl acrylate;

(ii) 24 to 32 percent by weight of methyl acrylate;

(iii) 2 to 8 percent by weight of acrylic acid;

(iv) 2 to 10 percent by weight of vinyl acetate; and (v) 0.5 to 3 percent by weight of hydroxyethyl acrylate.

4. The system of claim 1 wherein 1 $cm^2$ of the matrix comprises;

0.1 to 0.5 mg of octyldodecanol;

0.05 to 0.5 mg of oestradiol;

0.5 to 1.5 mg of norethisterone acetate; and 5 to 12 mg of the acrylate-based adhesive.

5. The system of claim 1 wherein the backing sheet is polyethylene terephthalate.

6. The system of claim 1 wherein the active ingredients are uncrystallized and dissolved.

* * * * *